(12) United States Patent
Hayakawa et al.

(10) Patent No.: US 8,595,666 B2
(45) Date of Patent: Nov. 26, 2013

(54) SEMICONDUCTOR DEFECT CLASSIFYING METHOD, SEMICONDUCTOR DEFECT CLASSIFYING APPARATUS, AND SEMICONDUCTOR DEFECT CLASSIFYING PROGRAM

(75) Inventors: Koichi Hayakawa, Hitachinaka (JP); Takehiro Hirai, Ushiku (JP); Yutaka Tandai, Hitachinaka (JP); Tamao Ishikawa, Hitachinaka (JP); Tsunehiro Sakai, Mito (JP); Kazuhisa Hasumi, Hitachinaka (JP); Kazunori Nemoto, Akishima (JP); Katsuhiko Ichinose, Tokorozawa (JP); Yuji Takagi, Kamakura (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/382,437

(22) PCT Filed: May 14, 2010

(86) PCT No.: PCT/JP2010/003259
§ 371 (c)(1),
(2), (4) Date: Feb. 7, 2012

(87) PCT Pub. No.: WO2011/004534
PCT Pub. Date: Jan. 13, 2011

(65) Prior Publication Data
US 2012/0131529 A1 May 24, 2012

(30) Foreign Application Priority Data

Jul. 9, 2009 (JP) .................................. 2009-162334

(51) Int. Cl.
G06F 17/50 (2006.01)

(52) U.S. Cl.
USPC ............................................................ 716/112

(58) Field of Classification Search
USPC ............................................................ 716/112
See application file for complete search history.

(56) References Cited

U.S. PATENT DOCUMENTS

| | | | |
|---|---|---|---|
| 6,799,130 B2 | 9/2004 | Okabe et al. | |
| 6,977,183 B1 * | 12/2005 | DiBiase | 438/7 |
| 7,869,966 B2 | 1/2011 | Okabe et al. | |
| 2005/0004774 A1 * | 1/2005 | Volk et al. | 702/108 |
| 2010/0005442 A1 * | 1/2010 | Ghinovker et al. | 716/21 |

FOREIGN PATENT DOCUMENTS

| | | |
|---|---|---|
| JP | 01-259245 A | 10/1989 |
| JP | 02-102404 A | 4/1990 |
| JP | 07-325044 A | 12/1995 |
| JP | 2003-86645 A | 3/2003 |

(Continued)

*Primary Examiner* — Jack Chiang
*Assistant Examiner* — Brandon Bowers
(74) *Attorney, Agent, or Firm* — Mattingly & Malur, PC

(57) ABSTRACT

A defect is efficiently and effectively classified by accurately determining the state of overlap between a design layout pattern and the defect. This leads to simple identification of a systematic defect. A defective image obtained through defect inspection or review of a semiconductor device is automatically pattern-matched with design layout data. A defect is superimposed on a design layout pattern for at least one layer of a target layer, a layer immediately above the target layer, and a layer immediately below the target layer. The state of overlap of the defect is determined as within the pattern, over the pattern, or outside the pattern, and the defect is automatically classified.

24 Claims, 9 Drawing Sheets

(56) References Cited

FOREIGN PATENT DOCUMENTS

| | | | |
|---|---|---|---|
| JP | 200910286 A | 1/2009 |
| JP | 2009-516835 A | 4/2009 |
| WO | 2007-120280 A2 | 10/2007 |

\* cited by examiner

Fig. 2

[INFORMATION]
~ Omission ~
Image magnification (Low)=8000
Image magnification (High)=15000
Image resolution (Low)=512
Image resolution (High)=512
    .
    .
[RESULT]
X coordinate of barycenter of defective region=230.000
Y coordinate of barycenter of defective region=235.500

11

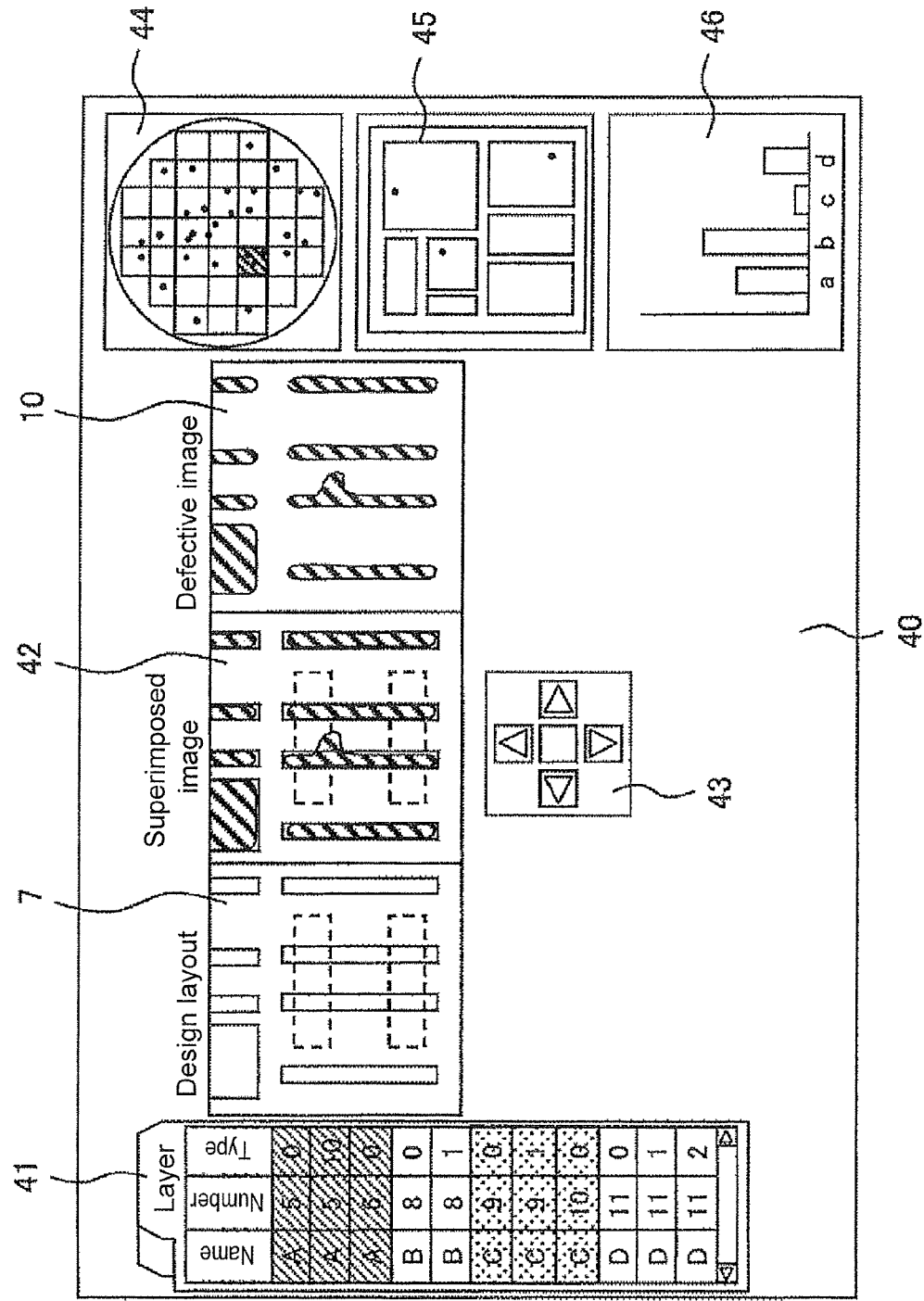

(a) Within pattern  (b) Over pattern  (c) Outside pattern (a)  (b)  (c)

SEMICONDUCTOR DEFECT CLASSIFYING METHOD, SEMICONDUCTOR DEFECT CLASSIFYING APPARATUS, AND SEMICONDUCTOR DEFECT CLASSIFYING PROGRAM

TECHNICAL FIELD

The present invention relates to a semiconductor defect classifying method, a semiconductor defect classifying apparatus, a program for a semiconductor defect classifying apparatus, a semiconductor defect inspecting method, and a semiconductor defect inspecting system for classifying defects including a systematic defect in a wafer or chip during a semiconductor device manufacturing process.

BACKGROUND ART

The major cause of reduction in wafer fabrication yield in the pre-process of semiconductor manufacturing has conventionally been a foreign matter appearing randomly on a semiconductor wafer, and the yield has been maintained by reducing foreign matters. However, in recent years, the minimum pattern line widths of semiconductor devices have been decreasing from 45 nm to 32 nm, and the proportion of design-layout-dependent defects is increasing.

Such a layout-dependent defect is called a systematic defect. Examples of a systematic defect include an abnormality in resistance caused by a variation in pattern shape resulting from a difference in level of an underlayer and faulty electrical continuity of a contact hole caused by insufficient etching at a specific region of a gate oxide film.

In order to reduce defects in semiconductor wafers, a semiconductor wafer is inspected by, e.g., a dark-field, bright-field, or electron-beam defect inspecting apparatus during the manufacture of the semiconductor wafer. A review apparatus acquires clear images of defects on the basis of information on the positions of the defects detected by any of the inspecting apparatuses. ADC (Automatic Defect Classification) that refers to automatically classifying a defect is performed on the basis of the images. Measures are taken against defects according to categories, into which defects are classified, and the frequency of defects.

However, the conventional ADC classification remains within classification into categories based on the shape, brightness, and the like of a defect observed with a review apparatus and cannot identify the cause of a layout-induced systematic defect. Accordingly, there has recently been a need for a technique for classifying a defect using design layout data.

Methods for checking a defect against design layout data have already been reported. Patent Literature 1 below discloses the process of superimposing a defective image on layout data and determining, on the basis of the position of a defect, information on the density of defects in a region, and the like, whether the defect is a systematic defect, in order to identify the cause of a defect.

CITATION LIST

Patent Literature

Patent Literature 1: JP Patent Publication (Kokai) No. 2009-10286 A (2009)

SUMMARY OF INVENTION

Technical Problem

Patent Literature 1 discloses the process of performing systematic defect classification by establishing in advance a defect classification definition for each region of patterns of a design layout and determining, on the basis of defect data or, more specifically, defect coordinates acquired from an inspection apparatus, in which pattern of the design layout the defect coordinates lie.

However, defect coordinates output from a defect inspecting apparatus have an error of several to over ten micrometers. In the case of a semiconductor device with a pattern width of less than 0.1 micrometer like a modern one, an erroneous determination may be made.

A defect is not a point and has two or three dimensions. Accordingly, even if the accuracy of defect coordinates is higher, it is difficult to accurately determine the state of overlap, i.e., whether a defect is completely within a pattern, extends across a boundary of the pattern, or is completely outside the pattern. A simple example of a difference in the state of overlap of a pattern playing an important role in identifying the cause of a defect is that a foreign matter appearing at a random position is highly likely to extend across a boundary of a pattern and a layout-induced systematic defect is highly likely to fit within a specific pattern.

It is an object of the present invention to determine the state of overlap between a target pattern of design layout data and a defect (whether the defect is within a pattern, over one or more patterns, or outside a pattern) by superimposing a defective image on the target pattern and comparing the defective image with the target pattern and provide a defect classifying method which is effective at identifying the cause.

Solution to Problem

In order to achieve the above-described object, according to the present invention, there is provided a defect classifying apparatus which pattern-matches a defective image of the defect at a target layer from the defect inspecting apparatus or the review apparatus with design layout data of the semiconductor device, superimposes the defect on a design layout pattern for at least one layer of the target layer, a layer immediately above the target layer, and a layer immediately below the target layer, determines the state of overlap of the defect, and classifies the defect.

According to the present invention, a defect shape image is generated from a difference between the defective image from the defect inspecting apparatus or the review apparatus and a reference image without the defect, the defect shape image is superimposed on the design layout pattern, the state of overlap of the defect is determined, and the defect is classified.

According to the present invention, a defect shape image is generated through pattern recognition of the defective image, the defect shape image is superimposed on the design layout pattern, the state of overlap of the defect is determined, and the defect is classified.

According to the present invention, defect coordinates are acquired from the defect inspecting apparatus or the review apparatus, a defect size is acquired from any one of the defect inspecting apparatus, the review apparatus, and the design layout pattern, the state of overlap of the defect is determined on the basis of a positional relationship of the defect coordinates in the design layout pattern and the defect size, and the defect is classified.

According to the present invention, an outline is extracted from the defect shape image, the outline is superimposed on the design layout pattern, the state of overlap of the defect is determined, and the defect is classified.

The state of overlap of the defect is determined as within the pattern, over the pattern, or outside the pattern, and the defect is classified.

According to the present invention, the state of overlap of the defect is determined as within the pattern, over the pattern, or outside the pattern on the basis of a ratio between a total area of the defect shape image and an area of a part within the pattern of the defect shape image, and the defect is classified.

According to the present invention, the state of overlap of the defect is determined as within the pattern, over the pattern, or outside the pattern on the basis of a ratio between length of the outline and length of a part protruding from a pattern, and the defect is classified.

According to the present invention, the design layout pattern is widened or contracted, the state of overlap of the defect is determined, and the defect is classified.

Advantageous Effects of Invention

According to the present invention, accurate determination of the state of overlap between a design layout pattern and a defect (within a pattern/over one or more patterns/outside a pattern) allows efficient and effective classification of defects and, additionally, identification of a systematic defect that is a problem for modern microdevices. Classification of such systematic defects leads to development and trial manufacture of semiconductor devices and rapid increase in the yield of semiconductor devices in mass production.

BRIEF DESCRIPTION OF DRAWINGS

FIG. 2 is a view showing an example of an image information file.

FIG. 4 is a view showing a user screen in a defect classifying apparatus.

DESCRIPTION OF EMBODIMENTS

Figure 1:
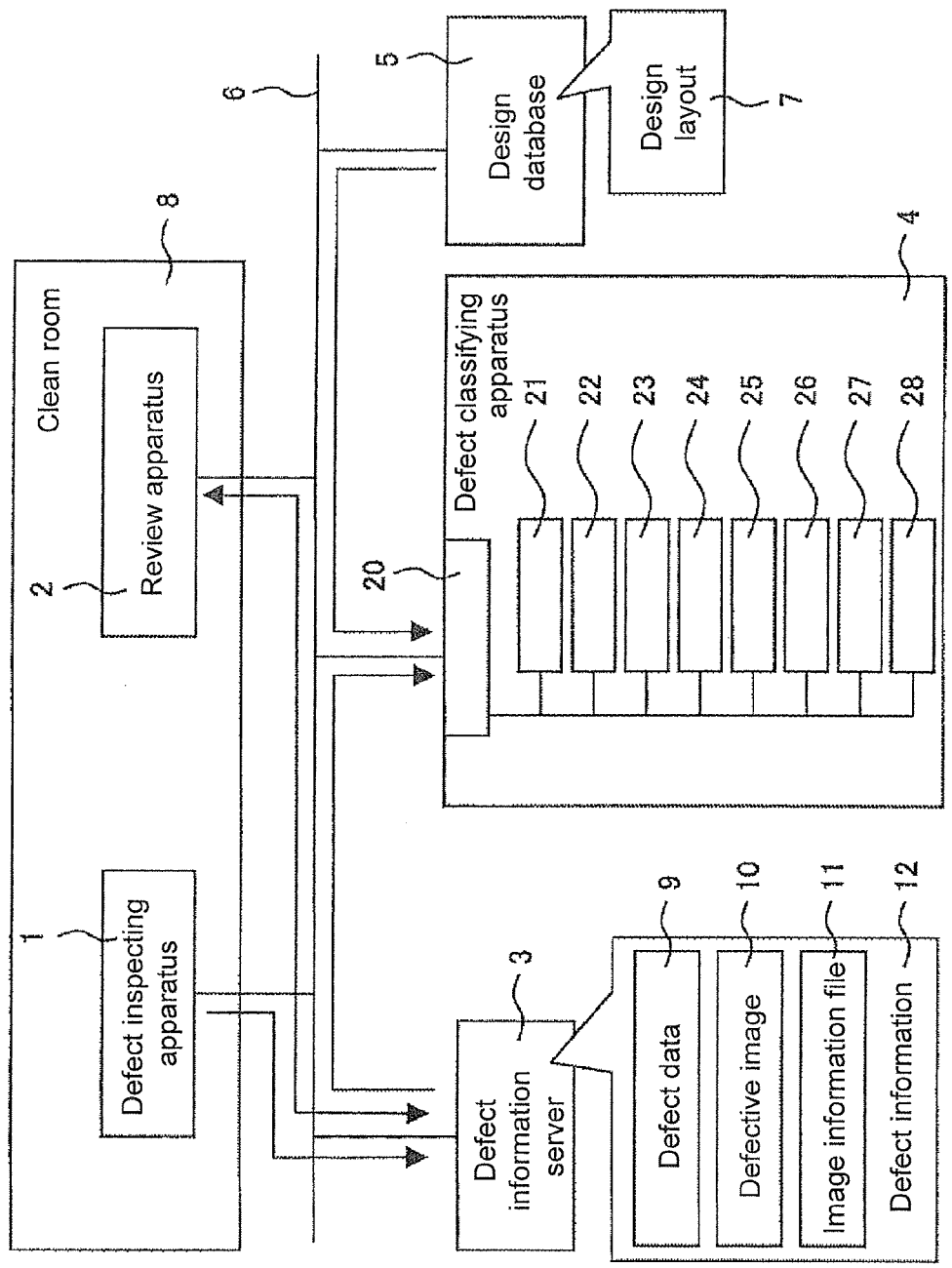
FIG. 1 is a diagram showing the overall configuration of the present invention.

An embodiment of the present invention will be described below with reference to the drawings.

The overall configuration of the present invention will be described with reference to FIG. 1. A semiconductor manufacturing process is generally performed in a clean room 8 in an environment kept clean. A defect inspecting apparatus 1 which inspects a finished wafer for defects is placed in the clean room 8. The defect inspecting apparatus 1 is, e.g., a dark-field defect inspecting apparatus, a bright-field defect inspecting apparatus, or an electron-beam defect inspecting apparatus. The defect inspecting apparatus 1 may have the function of detecting a defect appearing at the surface of a device to be inspected and simultaneously acquiring a review image of the detected defect (a defective image 10). A review apparatus 2 which observes a defect detected by the defect inspecting apparatus 1 on the basis of the coordinate information of the defect is placed in the clean room 8. An SEM defect review apparatus is mainly used as the review apparatus 2. A defect information server 3 which stores data for the defect inspecting apparatus 1 and data for the review apparatus 2 is also placed.

In the present embodiment, a defect classifying apparatus 4 and other apparatuses are connected over a communication network 6. A design database 5 is also connected to the communication network 6. The design database 5 stores a design layout 7 of a semiconductor device to be subjected to defect inspection. The design layout 7 is desirably in an industry standard format such as GDS-II or OASIS but is not limited to these formats. Since data simulating an ideal finished shape is suitable as the design layout 7, data without an OPC (Optical Proximity Correction) pattern or data obtained by predicting the condition of an actually finished pattern through a simulation, if possible, is desirable. However, the design layout 7 is not limited to the pieces of data.

The flow of data transmitted between the apparatuses in FIG. 1 will be described. A series of data including defect data 9 (including pieces of information such as the coordinates and category of a defect detected by the defect inspecting apparatus 1), the reviewed defective image 10 (including an image of each defect acquired by the defect inspecting apparatus 1 or review apparatus 2), and an image information file 11 (including pieces of information such as an image acquisition condition for the defective image 10) acquired by the defect inspecting apparatus 1 or review apparatus 2 will be referred to as defect information 12 and is transmitted to the defect information server 3.

In preparation for defect classification, the defect information 12 stored in the defect information server 3 is transmitted to the defect classifying apparatus 4. The design layout 7 of a target device is transmitted from the design database 5 to the defect classifying apparatus 4.

The system configuration of the defect classifying apparatus 4 in FIG. 1 will be described.

The defect classifying apparatus 4 is composed of, e.g., a workstation or personal computer and has the function of choosing systematic defects among defects detected by the defect inspecting apparatus 1 and review apparatus 2. More specifically, the defect classifying apparatus 4 includes a network interface 20 which transmits/receives data to/from another apparatus, a main storage 21 which stores the design layout 7, the defect information 12, and the like, a layout conversion calculating section 22 which performs graphics transformation so as to load the design layout 7 acquired from the design data server 5 into a system, a sampling section 23 which determines, on the basis of category information of the defect information 12, whether each defect is a target systematic defect, a matching section 24 which matches the defective image 10 with the design layout 7, a defect shape image extracting section 25 which generates a defect shape image from the difference between the defective image and a reference image without a defect or through pattern recognition of the defective image, a section 26 which superimposes the defective image 10 on the design layout 7, a defect classifying section 27 which determines the state of overlap between defects and a layout pattern and classifies the defects, a layout characteristic calculating section 28 which calculates layout characteristics such as the pattern density of the design layout 7, input devices such as a keyboard on which layout data or the like is displayed and through which an operator enters instructions and a mouse, and a display on which a user interface 29 is to be displayed.

The above-described functional sections such as the sampling section 23, matching section 24, defect shape image extracting section 25, superimposition section 26, defect classifying section 27, and layout characteristic calculating section 28 can be implemented in hardware or software. In the case of a hardware implementation, computing units implementing the functional sections are integrated onto a single substrate. In the case of a software implementation, a high-speed general purpose processor executes programs or codes corresponding to processes of the functional sections. The programs are stored in the main storage 21 or various types of memory (not shown).

The processing function of the defect classifying apparatus 4 may also be implemented using an FPGA (Field Programmable Gate Array) as an implementation intermediate between a hardware implementation and a software implementation. An implementation using an FPGA requires a logic circuit chip constituting the main body of the FPGA as well as a nonvolatile memory storing a program (which may also be referred to as configuration data) for providing circuits configured to implement processes necessary for the functional sections in the logic circuit chip. Note that the term program here refers to a program describing the circuits (corresponding to the functional sections) to be implemented on the FPGA and is different from a program in a software implementation.

Two or more of the hardware implementation, the software implementation, and the implementation using an FPGA described above may be adopted in combination. An example of this case is a case where some functions are implemented in hardware, and the other functions are implemented using an FPGA. If some of the functional sections that require high-speed processing, such as the layout conversion calculating section 22, matching section 24, and layout characteristic calculating section 28, are constructed using an FPGA, and some of the functional sections that require the flexible process of, e.g., referring to parameters for which different defect classification criteria are set for respective users, such as the defect classifying section 27, are implemented in software, the defect classifying apparatus 4 with high cost performance can be implemented.

Although the data transmission/reception shown in FIG. 1 is based on transmission/reception over a network, data can also be transmitted/received via a hard disk drive or a memory stick.

FIG. 2 shows an example of the image information file 11. The information is composed of the magnification information of defects, image resolutions, positions in an image where defects are detected, and the like acquired by the defect inspecting apparatus 1 and review apparatus 2. Since the magnification of the defective image 10 is determined at the time of acquisition of the image, when the defective image 10 is superimposed on the design layout 7, the magnification of the design layout 7 can be made equal to the magnification, at which the defective image 10 is acquired, by using the magnification information of defects included in the image information file 11.

Figure 3:
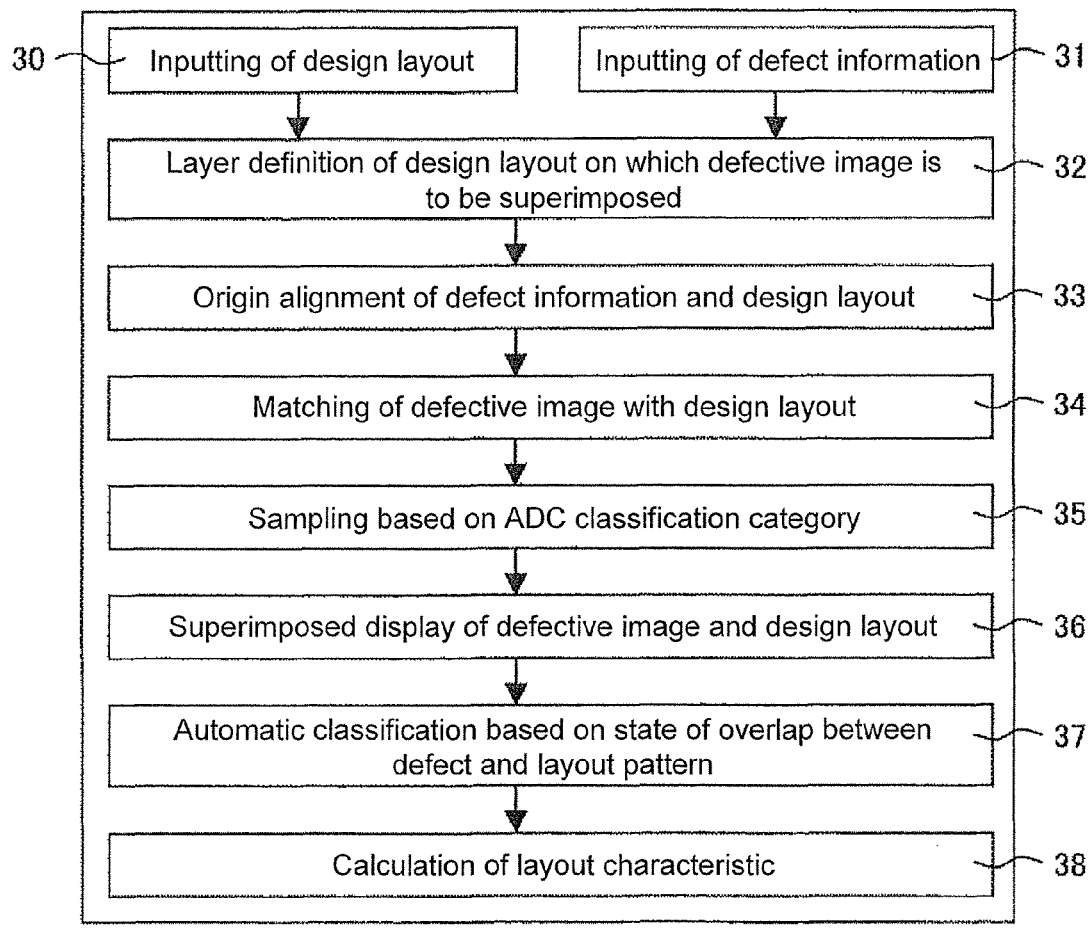
FIG. 3 is a chart showing a defect classifying procedure.

FIG. 3 is a chart showing a defect classifying procedure.

First, inputting 30 of the design layout 7 and inputting 31 of the defect information 12 are performed. Pre-processing including graphics transformation and format conversion is performed.

Layer definition 32 of the design layout 7 on which the defective image 10 is to be superimposed is performed. Since even a layer in one manufacturing process may be used for a plurality of layer numbers and a plurality of data types in the design layout 7, combination 32 of the pieces of data is performed for the one layer.

Origin alignment 33 of the defect information 12 and the design layout 7 is performed. The origin may be set at the center of a die in the design layout 7 while the origin may be set at the lower left corner of a die in the defect information 12. That is, the design layout 7 and defect information 12 may adopt different coordinate systems. Accordingly, the origin of the design layout 7 is registered at the same pattern position of the same place as the defect information 12.

Sampling 34 based on ADC classification categories is performed by the review apparatus, as needed. For example, it is effective to filter random defects resulting from a foreign matter and a scratch and the like and extract only defects belonging in categories associated with systematic defects such as a short defect and an open defect.

Matching 35 of the defective image 10 with the design layout 7 is performed for each defect. The process origin alignment 33 causes the defective image 10 and design layout 7 to have the same coordinate system, and the defective image 10 is moved to a corresponding position of the design layout 7 on the basis of a position where a defect is detected. Since the position of a defect is often deviated from a corresponding position on design data, pattern matching is performed here while a search is made within a range wider than the field of view of an acquired image. The design layout 7 used for the matching 35 may be data for the entire chip or data for a part of a fixed size or the size of the defective image 10 cut out about a position where a defect is detected, i.e., a layout for a limited region. For example, the design layout 7 may be data for a region of a size 1.5 or 2 times that of the defective image that is determined to allow for a deviation in coordinates. Alternatively, a possible value of a deviation in coordinates may be examined in advance, and the design layout 7 for a region of a size larger than the size of the defective image 10 by an amount enough to cover the value may be cut out. The process of moving the design layout 7 for a region equal to or smaller than the defective image on the defective image 10 to perform matching is also possible. In addition to the illustrated methods, some combinations are conceivable. Note that the sampling 34 and the matching 35 may be performed in the reverse order.

Superimposed display 36 of the defective image 10 of a given defect and a given layer of the design layout 7 is performed. The term given layer here refers to a layer to be inspected or another layer higher or lower than the layer. A plurality of layers can be selected as the given layer. Effects of defects on layers can be visually checked by selecting all layers or ones likely to be the major cause of a defect of the design layout 7 and displaying the layers in a superimposed manner.

Automatic classification 37 based on the state of overlap between defects and a layout pattern is performed using the defective image 10 and design layout 7. For example, if a layer to be inspected is a poly-Si layer, defects can be classified in detail using a layer with an N-type or P-type active region or field region or a region with a withstand voltage different from that of a general MOS (e.g., a high withstand voltage region) lower than the poly-Si layer or can be classified on the basis of pattern information including a cell, a peripheral circuit, and a dummy pattern.

Finally, calculation 38 of layout characteristics such as the pattern density, area ratio, minimum space dimension, and minimum line width at or near the defect is performed. The process of calculating such layout characteristics and seizing a statistical trend, for each of defect types into which defects are finally classified in the present embodiment, is very effective at analyzing a systematic defect. Comparison of the statistical trend of each defect type with the pattern density, area ratio, minimum space dimension, and minimum line width of the entire chip brings a statistical feature into more sharp relief. For example, if the pattern density at or near a defect for one of the defect types tends to be high in the pattern density distribution of the entire chip, it is apparent that a defect of this type is likely to appear in a region dense with patterns. As described above, calculation of the layout characteristics of the entire chip is also very effective. To elicit a systematic defect by classifying defects when an underlayer layout is composed of a P-type diffusion layer with a general MOS withstand voltage, when the underlayer layout is composed of an N-type diffusion layer with a general MOS withstand voltage, when the underlayer layout is composed of a P-type diffusion layer of a high withstand voltage MOS, and when the underlayer layout is composed of an N-type diffusion layer of a high withstand voltage MOS, as in the case of a contact failure, comparison with the existence probability of contacts at each layer with respect to the entire chip is also effective. For example, if the rate of occurrence of contact failures at the P-type diffusion layer of the high withstand voltage MOS as the underlayer layout is high relative to the ratio of contacts located at the P-type diffusion layer of the high withstand voltage MOS to contacts of the entire chip, it is apparent that the P-type diffusion layer of the high withstand voltage MOS has a high percentage of contact failures, i.e., the major cause of a systematic failure exists at the P-type diffusion layer. As described above, the process of obtaining the existence probability of contacts at each layer is very important by analyzing the layout of the entire chip.

With results of the above-described calculations, whether a defect is a systematic defect can also be determined.

Note that the order of the sampling 34, matching 35, superimposed display 36, automatic classification 37, and layout characteristic calculation 38 may be changed according to the intended use and that the order is not limited to the one shown in FIG. 1.

FIG. 4 shows a user screen 40 in the defect classifying apparatus 4. On the left of the screen, a window 41 is displayed where the layer definition 32 of the design layout 7, on which the defective image 10 in FIG. 3 is to be superimposed, is performed. In the window, defined target layer numbers and data types can be confirmed and changed. A list of defects can be displayed by, e.g., switching to another tab. The defect sampling can also be implemented in this window.

Three windows are simultaneously displayed at the center of the screen. The defective image 10 acquired at the time of review is displayed in the window on the right, the design layout 7 for the same position as a position where a defect is detected is displayed on the left, and a superimposed image 42 of the two images is displayed at the center. By displaying the three windows, the matching state of layout data and a review image can be confirmed at a glance. It is also effective here to set one of the regions for the defective image 10 and design layout 7 as a base and not to display a protruding part of a pattern. The display in the three windows allows simultaneous display of a plurality of layers to be matched. It is possible to confirm the interaction between layers while checking a target layer with an image.

If automatic matching is unsuccessful, a layout image can be manually moved and superimposed, and adjustment can be performed again. In this case, the position of the defective image 7 is set as a basic position. The design layout 10 is shifted while move buttons (up, down, left, and right buttons) 43 are clicked and is superimposed on the defective image.

A wafer map based on defect coordinates detected by the defect inspecting apparatus 1 is displayed as a wafer map 44. In a die map 45, in which part of a die a defect is present can be confirmed, and the positional relationship between a spot where each defect appears and circuit blocks in a semiconductor device such as a control circuit section, an arithmetic circuit section, and a RAM section can be confirmed. A defect displayed in the three windows at the center of the screen can also be highlighted in the wafer map 44 and die map 45. A defect desired to be viewed can be displayed in the three windows at the center of the screen by clicking the defect in the wafer map 44 or die map 45. A result of ADC classification categories or a result of classification by the defect classifying apparatus 4 can be graphed as a graphical representation 46.

A procedure for preparation for automatic defect classification based on the state of overlap between a defect and a layout pattern will be described.

Figure 5A:
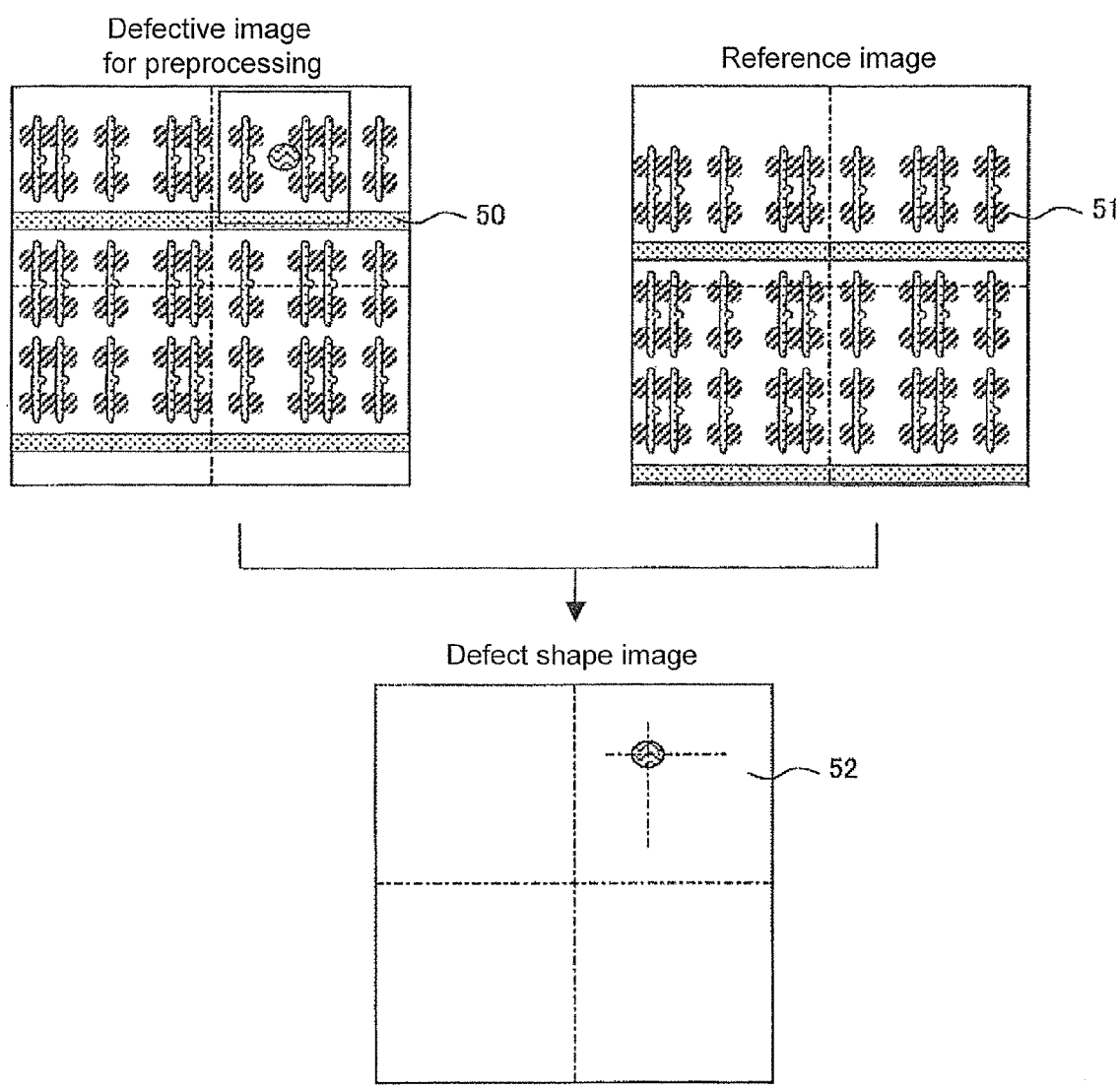
FIG. 5(A) is a view showing a method for acquiring a defect shape image.

FIG. 5(A) is a view showing a method for acquiring a defect shape image 52. A method for acquiring only the defect shape image 52 from the difference between a defective image 50 for preprocessing and a reference image 51 without a defect will be described with reference to FIG. 5(A).

The defective image 50 for preprocessing may be identical to the defective image 10 or may be an image at lower magnification than the defective image 10. Note that, at the time of pattern matching of the defective image 50 for preprocessing with the reference image 51, the magnification of the defective image 50 for preprocessing is made as equal to that of the reference image 51 as possible or the magnification of one is made equal to that of the other image by digital zooming. After the matching, the difference between the images is obtained. A pixel with a difference in gray level larger than a specified threshold value is regarded as a defective region or such pixels, the number of which is larger than a fixed pixel number, are regarded as a defective region. The defect shape image 52 including a defective region is generated. At this time, the defect shape image 52 may be a binary image or may be converted into an image with a small number of gray levels.

Figure 5B:
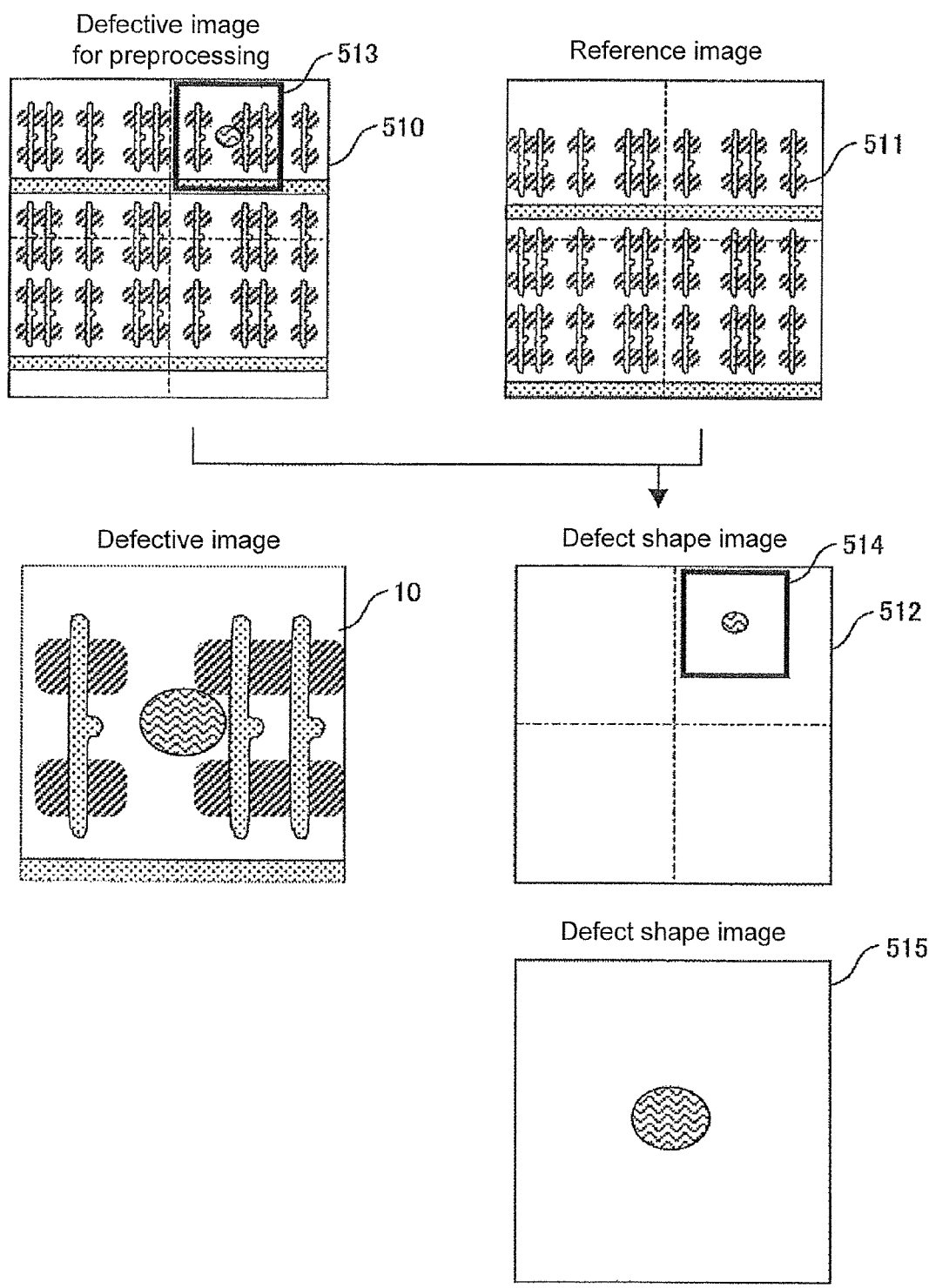
FIG. 5(B) is a view showing a method for acquiring a detect shape image.

FIG. 5(B) is a view showing a second method that is a method for acquiring the defect shape image 52. A defective image 510 for preprocessing is an image picked up at lower magnification than the defective image (defect review image) 10. A reference image 511 is close in magnification to the defective image 510 for preprocessing enough for pattern matching. After matching, the difference between the images is obtained. A pixel with a difference in gray level larger than a specified threshold value is regarded as a defective region or such pixels, the number of which is larger than a fixed pixel number, are regarded as a defective region. A defect shape image 512 including a defective region is generated. The defective image 10 is an image picked up while a part indicated by a region 513 of the defective image 510 for preprocessing is magnified. Accordingly, a defect shape image 515 generated by magnifying a region 514 on the defect shape image 512 corresponding to the region 513 to the same level as the defective image 10 by image processing can be used as the defect shape image 52 to be superimposed on the design layout 7.

Figure 5C:
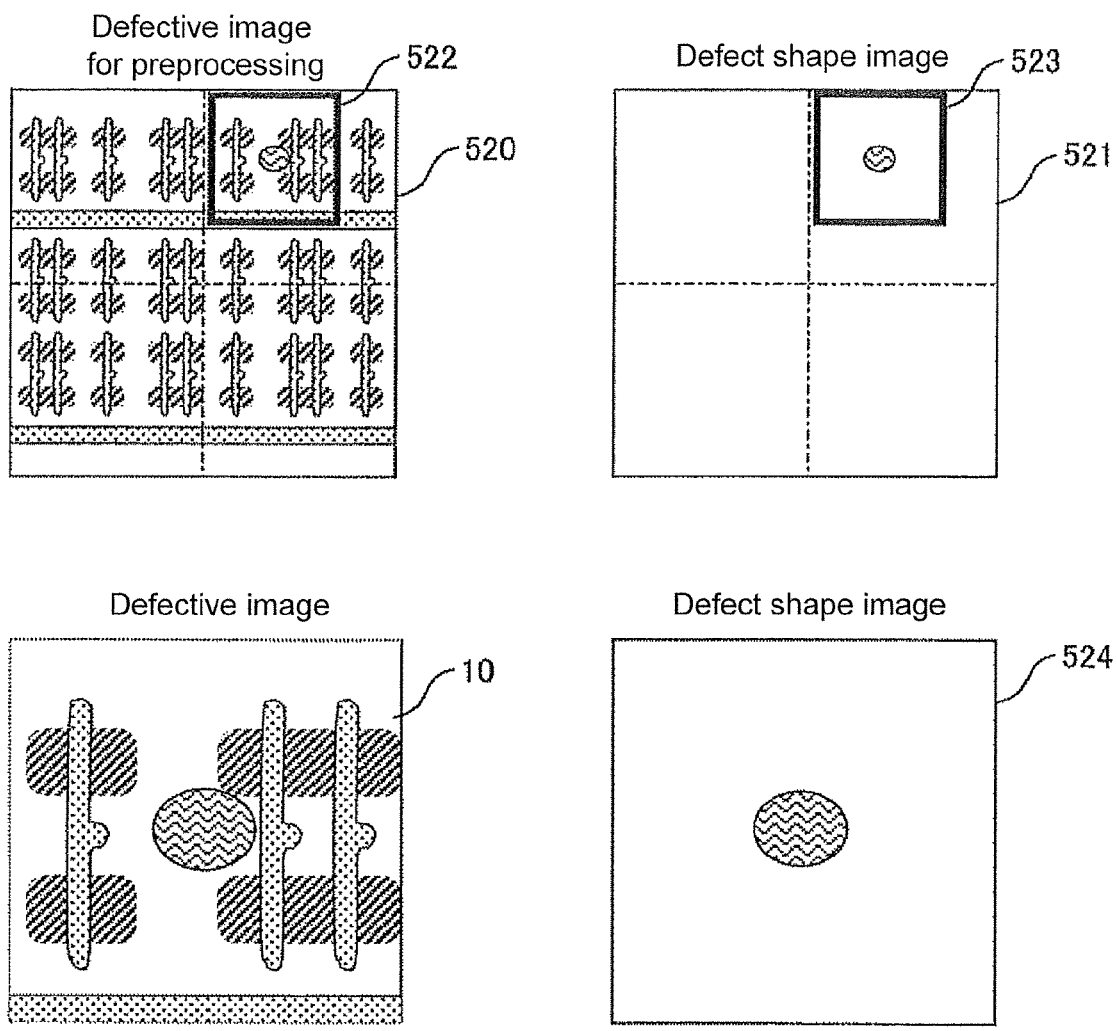
FIG. 5(C) is a view showing a method for acquiring a detect shape image.

FIG. 5(C) is a view showing a third method that is a method for acquiring the defect shape image 52. A defective image 520 for preprocessing is an image picked up at lower magnification than the defective image (defect review image) 10.

Assume that an object to be reviewed is an SRAM region, DRAM region, or flash memory region incorporated in a system LSI or an SRAM, DRAM, or flash memory as a semiconductor product. If a reviewed region where a defect appears is a repeating pattern region, a defect shape image 521 can be obtained by taking advantage of the repeatability of the pattern of the region. The defective image 10 is an image picked up while a part indicated by a region 522 of the defective image 520 for preprocessing is magnified. Accordingly, a defect shape image 524 generated by magnifying a region 523 on the defect shape image 521 corresponding to the region 522 to the same level as the defective image 10 by image processing can be used as the defect shape image 52 to be superimposed on the design layout 7.

If a region where a defect appears is not a complete repeating pattern region, the defect shape image 521 can be generated from the defective image 520 for preprocessing by, e.g., the method below. The method includes dividing the defective image 520 for preprocessing into local regions, matching each local region with local regions of an already stored image, obtaining the difference between the local regions matching each other, and extracting a defective region.

It is also possible to generate the defect shape image 521 from the defective image 520 for preprocessing by using an algorithm for automatically detecting an abnormality in a given image.

Figure 6:
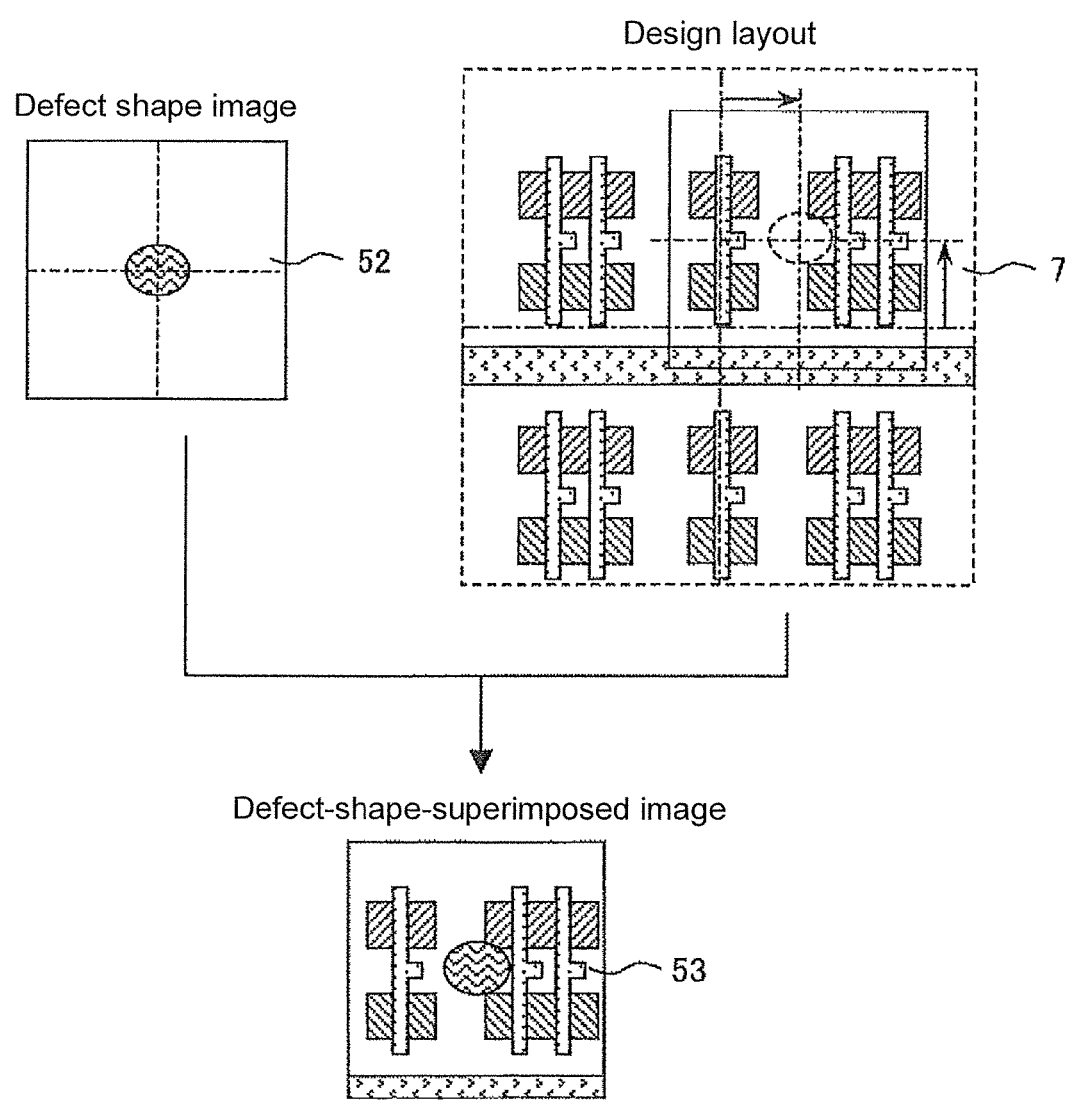
FIG. 6 is a view showing a procedure for superimposing a defect shape image on a design layout.

FIG. 6 is a view showing a procedure for superimposing the defect shape image 52 on the design layout 7. The defect shape image 52 is superimposed on the design layout 7 on the basis of the matching positional relationship between the defective image 10 and the design layout 7 and the positional relationship between the defective image 10 and the defective image 50 for preprocessing. The magnifications of the design layout 7 and defect shape image 52 are made equal in advance. The superimposition results in generation of the defect-shape-superimposed image 53.

Although not shown, simple superimposition which does not require accuracy will be described. In this case, if the coordinates and the size of a defect are known, it is possible to assume that the shape of the defect is, e.g., circular and virtually draw the defect shape so as to be superimposed on the design layout 7. The defect size can be acquired from the defect inspecting apparatus 1 or review apparatus 2. After hole formation and filling in a contact process or via process, in the case of faulty electrical continuity, a contact portion or via portion may exhibit an abnormal contrast. In the process, if the coordinates of a defect and the diameter of a hole are known, an image can be generated on the basis of the pieces of information and can be superimposed. In this case, a defect size may be acquired from any one of the defect inspecting apparatus 1, review apparatus 2, and the design layout 7.

Although not shown, the defect shape image 52 can be generated through pattern recognition of the defective image 10. The pattern recognition is the general process of setting the number of layers for patterns in advance, identifying a pattern present in the defective image 10 for each layer on the basis of the number, extracting an expanded part, a contracted part, and an isolated part of each pattern from irregularity or discontinuity of the image, and regarding the parts as defects. It is also effective to generate the defect shape image 52 through the extraction.

Although not shown, if a reviewed region where a defect appears is a repeating pattern region in an SRAM region, DRAM region, or flash memory region incorporated in a system LSI or an SRAM, DRAM, or flash memory as a semiconductor product, it is also effective to use the process of analyzing the repeatability of the pattern of the region from a normal image region other than a region affected by a defect, presuming a normal image of the region affected by the defect, and virtually generating the reference image 51.

A method for generating the defect shape image 52 from the defective image 10 of a region with an aperiodic pattern of a semiconductor may include dividing the defective image 10 into local regions, matching each local region with local regions of an already stored image, obtaining the difference between the local regions matching each other, and extracting a defective region. Alternatively, the defect shape image 52 can be generated from the defective image 10 by using an algorithm for automatically detecting an abnormality in a given image.

With the above-described procedure, preparation for classification of the state of overlap between a pattern of the design layout and a defect is completed.

A method for classifying the state of overlap between a design layout and a defect will be described.

Figure 7:
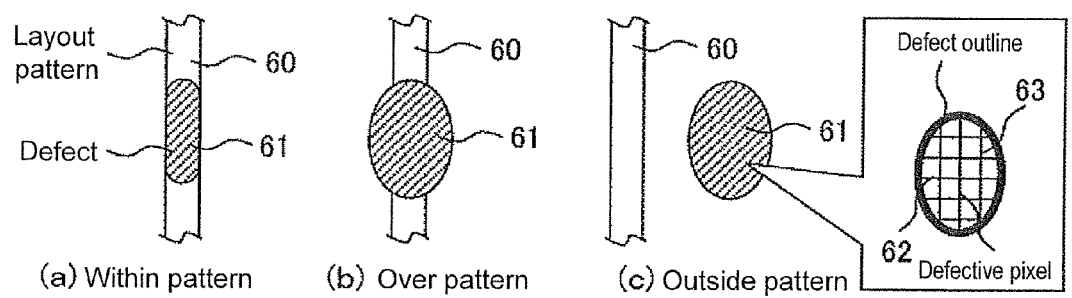
FIG. 7 are views showing a method for classifying and defining the state of overlap between a layout pattern and a defect.

FIG. 7 are views showing a method for classifying and defining the state of overlap between a layout pattern 60 and a defect 61 and is generated by superimposing the defect shape image 52 on the design layout 7. A defect is determined to be within a pattern, over the pattern, or outside the pattern on the basis of which one of the three states below the defect is in.

The category of "within a pattern" in FIG. 7(*a*) refers to a category for the defect 61 that is present within the layout pattern 60 without protruding from the layout pattern 60.

The category of "over a pattern" in FIG. 7(*b*) refers to a category for the defect 61 that is present so as to extend across and protrude from the layout pattern 60.

The category of "outside a pattern" in FIG. 7(*c*) refers to a category for the defect 61 that is present so as not to overlap with the layout pattern 60.

The determination can be implemented by, for example, converting the layout pattern 60 into pixel information and checking each defective pixel 62 of the defect 61 with each pixel of the layout pattern 60. The determination can also be implemented by extracting a defect outline 63 which is the outer extremity of the defect 61 and checking the defect outline 63 with the layout pattern 40.

Assume a case where a defect classified as within a pattern as shown in FIG. 7(*a*) is classified in more detail on the basis of whether the defect is in contact with the edge of a pattern. The finer classification can be performed by identifying pixels on the edge of the layout pattern 60 in advance and determining whether the defective pixels 62 of the defect 61 or the defect outline 63 that is the outer extremity of the defect 61 overlaps with the identified pixels.

Similarly, assume a case where a defect classified as outside a pattern as shown in FIG. 7(*c*) is classified in more detail on the basis of whether the defect is in contact with the edge of a pattern. The finer classification can be performed by identifying pixels on the edge of the layout pattern 60 in advance and determining whether the defective pixels 62 of the defect 61 or the defect outline 63 that is the outer extremity of the defect 61 overlaps with the identified pixels.

Although the state of overlap is determined from the design layout 7 at the same layer as in the process of reviewing the defect 61 in the example in FIG. 7, classification may also be performed on the basis of the state of overlap with a layout pattern at any other layer. It is further effective to extract a systematic defect using a combination of classification results at a plurality of layers.

It is further effective to discriminate the state of overlap with a plurality of layout patterns, such as a bridge defect, from the state of overlap with one layout pattern and establish a defect classification category for the state.

The above-described classification is based on the premise that the defect shape image 52 is generated from the defective image 10 with accuracy and that the defect shape image 52 can be superimposed on the design layout 7 with accuracy. However, actually, the defect 61 may be generated to be larger or smaller than an actual defect or a positional deviation may occur at the time of superimposing the defect shape image 52 on the design layout 7. A method for coping with the problems will be described below.

Figure 8:
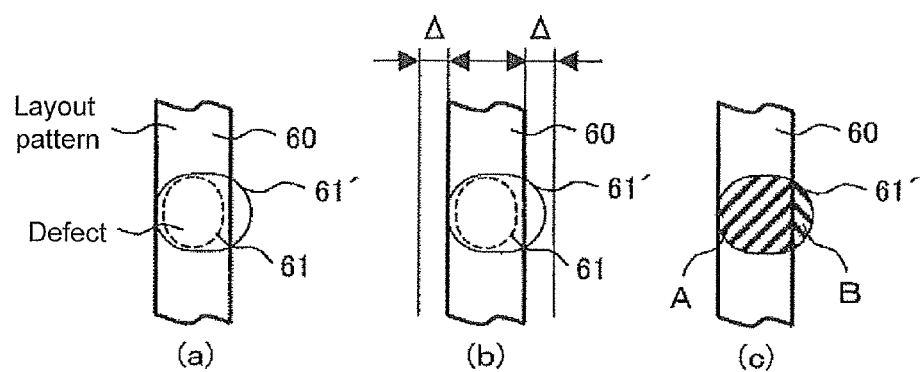
FIG. 8 are views showing a method for improving classification accuracy.

FIG. 8 are views showing a method for improving classification accuracy.

FIG. 8(*a*) shows the layout pattern 60 and a defect 61' having a shape error. The shape of the actual defect 61 is indicated by a dotted line. In the case in FIG. 8(*a*), the defect 61' having the shape error protrudes from the layout pattern 60 and may be erroneously classified as over a pattern. The defect 61' should actually be classified as within a pattern.

FIG. 8(*b*) shows a method for widening the layout pattern 60 to accommodate the shape error and is a view of the layout pattern 60 widened by Δ. According to the method, the defect 61' having the shape error can also be classified as with a pattern. The layout pattern widening method can also be applied to discrimination of a systematic defect appearing at a spot at a fixed distance from a layout pattern. In this case, a layout pattern is similarly widened by the fixed distance. By compiling defects classified as over a pattern or within a pattern, systematic defects can be detected.

FIG. 8(*c*) shows a method for improving classification accuracy by calculating the area ratio of the defect 61' having the shape error. Let A be an area by which the defect 61' having the shape error overlaps with the layout pattern 60, and B, an area of a protruding part. The classification accuracy can be improved by determining the defect as within a pattern if the ratio of the overlapping area A to the total area (A+B) of the defect is not less than a specified threshold value.

Although not shown, assume a case using the defect outline 63 (shown in FIG. 7). In this case, the defect is determined as within a pattern if the length of the outline of a part protruding from the layout pattern 60 is not more than a specified threshold value. Alternatively, whether the ratio of the length of the outline of a protruding part to the length of the entire outline may be determined.

Note although a case where a defect within a pattern is erroneously determined as a defect over a pattern has been described above, a similar concept can be applied to a case where a defect outside a pattern is erroneously determined as a defect over a pattern. In this case (not shown), the layout pattern 60 can be contracted. Alternatively, if the ratio of the overlapping area A to the total area (A+B) is not more than a different specified threshold value, the defect can be determined as outside a pattern. Two or more of the accuracy improving methods may also be used in combination.

As has been described above, according to the present invention, accurate determination of the state of overlap between a design layout pattern and a defect (within a pattern/over a pattern/outside a pattern) allows efficient and effective classification of defects and, additionally, identification of a systematic defect that is a problem for modern microdevices. Classification of such systematic defects leads to development and trial manufacture of semiconductor devices and rapid increase in the yield of semiconductor devices in mass production.

Reference Signs List
1 defect inspecting apparatus
2 review apparatus
3 defect information server
4 defect classifying apparatus
5 design database
6 communication network
7 design layout
8 clean room
9 defect data
10 defective image
11 image information file
12 defect information
20 network interface
21 main storage
22 layout conversion calculating section
23 sampling section
24 matching section
25 defect shape image extracting section
26 superimposition section
27 defect classifying section
28 layout characteristic calculating section
29 user interface

The invention claimed is:

1. A semiconductor defect classifying method for a defect classifying apparatus for classifying a defect of a semiconductor device by a defect inspecting apparatus which detects the defect and a review apparatus for observation, the method comprising:

the defect classifying apparatus performing pattern matching of a defective image of the defect at a layer to be inspected from the defect inspecting apparatus or the review apparatus with design layout data of the semiconductor device;

superimposing the defect on a design layout pattern of at least one of the layer to be inspected, a layer immediately above the layer to be inspected, and a layer immediately below the layer to be inspected;

determining the state of overlap between the defect and the layout pattern of the arbitrarily selected layer and automatically classifying the defect;

generating a defect shape image through pattern recognition of the defective image;

superimposing the defect shape image on the design layout pattern;

determining the state of overlap between the defect and the layout pattern of the arbitrarily selected layer and automatically classifying the defect;

extracting an outline from the defect shape image;

superimposing the outline on the design layout pattern; and determining the state of overlap of the defect and the state of overlap between the defect and the layout pattern of the arbitrarily selected layer and automatically classifying the defect.

2. The semiconductor defect classifying method according to claim 1, the method further comprising:

generating a defect shape image from a difference between the defective image and a reference image without the defect;

superimposing the defect shape image on the design layout pattern; and determining the state of overlap between the defect and the layout pattern of the arbitrarily selected layer and automatically classifying the defect;

3. The semiconductor defect classifying method according to claim 2, the method further comprising:

determining the state of overlap of the defect by determining the state of overlap between the defect and the layout pattern of the arbitrarily selected layer as within the pattern, over the pattern, or outside the pattern on the basis of a ratio between a total area of the defect shape image and an area of a part within the pattern of the defect shape image and automatically classifying the defect.

4. The semiconductor defect classifying method according to claim 1, the method further comprising:
   acquiring defect coordinates from the defect inspecting apparatus or the review apparatus;
   acquiring a defect size from any one of the defect inspecting apparatus, the review apparatus, and the design layout pattern; and
   determining the state of overlap between the defect and the layout pattern of the arbitrarily selected layer on the basis of a positional relationship of the defect coordinates in the design layout pattern and the defect size and automatically classifying the defect.

5. The semiconductor defect classifying method according to claim 1, the method further comprising:
   determining the state of overlap of the defect by determining the state of overlap between the defect and the layout pattern of the arbitrarily selected layer as within the pattern, over the pattern, or outside the pattern and automatically classifying the defect.

6. The semiconductor defect classifying method according to claim 1, the method further comprising:
   determining the state of overlap of the defect by determining the state of overlap between the defect and the layout pattern of the arbitrarily selected layer as within the pattern, over the pattern, or outside the pattern on the basis of a ratio between length of the outline and length of a part protruding from the pattern and automatically classifying the defect.

7. The semiconductor defect classifying method according to claim 1, the method further comprising:
   widening or contracting the design layout pattern; and
   determining the state of overlap between the defect and the layout pattern of the arbitrarily selected layer and automatically classifying the defect.

8. The semiconductor defect classifying method according to claim 1, the method further comprising
   statistically extracting a systematic defect by comparing a classification defect result of the defect or any one of a pattern density, an area ratio, a minimum space dimension, and a minimum line width at or near the defect with a trend in the defect or the one of an entire chip.

9. A defect classifying apparatus for classifying a defect of a semiconductor device by a defect inspecting apparatus which detects the defect and a review apparatus for observation, the defect classifying apparatus comprising:
   a section which receives inputting of a design layout;
   a section which receives inputting of defect information output from the defect inspecting apparatus or the review apparatus;
   a section which receives specification of a layer for a pattern of the design layout, on which a defective image included in the defect information is to be superimposed;
   a section which receives origin alignment setting of the defect information and the design layout pattern;
   a section which performs pattern matching of the defective image with the design layout pattern;
   a section which performs automatic classification on the basis of the state of overlap between the defect and the layout pattern of the arbitrarily specified layer;
   a section which generates a defect shape image through pattern recognition Of the defective image;
   a section which superimposes the defect shape image on the design layout pattern, determines the state of overlap between the defect and the layout pattern of the arbitrarily specified layer, and automatically classifies the defect;
   a section which extracts an outline from the defect shape image; and
   a section which superimposes the outline on the design layout pattern, determines the state of overlap between the defect and the layout pattern of the arbitrarily specified layer, and automatically classifies the defect.

10. The semiconductor defect classifying apparatus according to claim 9, the defect classifying apparatus further comprising:
    a section which generates a defect shape image from a difference between the defective image and a reference image without the defect;
    a section which superimposes the defect shape image on the design layout pattern, determines the state of overlap between the defect and the layout pattern of the arbitrarily specified layer, and automatically classifies the defect.

11. The semiconductor defect classifying apparatus according to claim 10, the defect classifying apparatus further comprising
    a section which determines the state of overlap of the defect by determining the state of overlap between the defect and the layout pattern of the arbitrarily specified layer as within the pattern, over the pattern, or outside the pattern on the basis of a ratio between a total area of the defect shape image and an area of a part within the pattern of the defect shape image and automatically classifies the defect.

12. The semiconductor defect classifying apparatus according to claim 9, the defect classifying apparatus further comprising:
    a section which acquires defect coordinates from the defect inspecting apparatus or the review apparatus;
    a section which acquires a defect size from any one of the defect inspecting apparatus, the review apparatus, and the design layout pattern; and
    a section which determines the state of overlap between the defect and the layout pattern of the arbitrarily specified layer on the basis of a positional relationship of the defect coordinates in the design layout pattern and the defect size and automatically classifies the defect.

13. The semiconductor defect classifying apparatus according to claim 9, the defect classifying apparatus, further comprising
    a section which causes execution of a section which determines the state of overlap of the defect by determining the state of overlap between the defect and the layout pattern of the arbitrarily specified layer as within the pattern, over the pattern, or outside the pattern and automatically classifying the defect.

14. The semiconductor defect classifying apparatus according to claim 9, the defect classifying apparatus further comprising
    a section which determines the state of overlap of the defect by determining the state of overlap between the defect and the layout pattern of the arbitrarily specified layer as within the pattern, over the pattern, or outside the pattern on the basis of a ratio between length of the outline and length of a part protruding from the pattern and automatically classifies the defect.

15. The semiconductor defect classifying apparatus according to claim 9, the defect classifying apparatus further comprising
a section which widens or contracts the design layout pattern; and
determines the state of overlap between the defect and the layout pattern of the arbitrarily specified layer and automatically classifies the defect.

16. The semiconductor defect classifying apparatus according to claim 9, the defect classifying apparatus further comprising
a section which compares a classification defect result of the defect or any one of a pattern density, an area ratio, a minimum space dimension, and a minimum line width at or near the defect with a trend in the result or the one of an entire chip.

17. A non-transitory computer readable medium storing a defect classifying program for classifying a defect of a semiconductor device by a defect inspecting apparatus which detects the defect and a review apparatus for observation, the defect classifying program causing execution of the steps of:
receiving inputting of a design layout;
receiving inputting of defect information output from the defect inspecting apparatus or the review apparatus;
receiving specification of a layer for a pattern of the design layout, on which a defective image included in the defect information is to be superimposed;
receiving origin alignment setting of the defect information and the design layout pattern;
performing pattern matching of the defective image with the design layout pattern;
performing automatic classification on the basis of the state of overlap between the defect and the layout pattern of the arbitrarily specified layer;
generating a defect shape image through pattern recognition of the defective image;
superimposing the defect shape image on the design layout pattern, determining the state of the overlap between the defect and the layout pattern of the arbitrarily specified layer, and automatically classifying the defect;
extracting an outline from the defect shape image; and
superimposing the outline on the design layout pattern, determining the state of overlap between the defect and the layout pattern of the arbitrarily specified layer, and automatically classifying the defect.

18. The non-transitory computer readable medium storing a semiconductor defect classifying program according to claim 17, the defect classifying program further causing execution of the steps of:
generating a defect shape image from a difference between the defective image and a reference image without the defect; and
superimposing the defect shape image on the design layout pattern, determining the state of overlap between the defect and the layout pattern of the arbitrarily specified layer, and automatically classifying the defect.

19. The non-transitory computer readable medium storing a semiconductor defect classifying program according to claim 18, the defect classifying program further causing execution of the steps of
determining the state of overlap of the defect by determining the state of overlap between the defect and the layout pattern of the arbitrarily specified layer as within the pattern, over the pattern, or outside the pattern on the basis of a ratio between a total area of the defect shape image and an area of a part within the pattern of the defect shape image and automatically classifying the defect.

20. The non-transitory computer readable medium storing a semiconductor defect classifying program according to claim 17, the defect classifying program further causing execution of the steps of:
acquiring defect coordinates from the defect inspecting apparatus or the review apparatus;
acquiring a defect size from any one of the defect inspecting apparatus, the review apparatus, and the design layout pattern; and
determining the state of overlap between the defect and the layout pattern of the arbitrarily specified layer on the basis of a positional relationship of the defect coordinates in the design layout pattern and the defect size and automatically classifying the defect.

21. The non-transitory computer readable medium storing a semiconductor defect classifying program according to claim 17, the defect classifying program further causing execution of the steps of
causing execution of the step of determining the state of overlap of the defect by determining the state of overlap between the defect and the layout pattern of the arbitrarily specified layer as within the pattern, over the pattern, or outside the pattern and automatically classifying the defect.

22. The non-transitory computer readable medium storing a semiconductor defect classifying program according to claim 17, the defect classifying program further causing execution of the steps of
determining the state of overlap of the defect by determining the state of overlap between the defect and the layout pattern of the arbitrarily specified layer as within the pattern, over the pattern, or outside the pattern on the basis of a ratio between length of the outline and length of a part protruding from the pattern and automatically classifying the defect.

23. The non-transitory computer readable medium storing a semiconductor defect classifying program according to claim 17, the defect classifying program further causing execution of the steps of
determining the state of overlap between the defect and the layout pattern of the arbitrarily specified layer by widening or contracting the design layout pattern and automatically classifying the defect.

24. The non-transitory computer readable medium storing a semiconductor defect classifying program according to claim 17, the defect classifying program further causing execution of the steps of
comparing a classification defect result of the defect or any one of a pattern density, an area ratio, a minimum space dimension, and a minimum line width at or near the defect with a trend in the defect or the one of an entire chip.

* * * * *